US00PP18691P3

(12) United States Plant Patent
Meilland

(10) Patent No.: US PP18,691 P3
(45) Date of Patent: Apr. 1, 2008

(54) HYBRID TEA ROSE PLANT NAMED 'MEIWIMOVA'

(50) Latin Name: *Rosa hybrida*
Varietal Denomination: Meiwimova

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 180 days.

(21) Appl. No.: 11/269,715

(22) Filed: Nov. 9, 2005

(65) Prior Publication Data

US 2007/0107104 P1 May 10, 2007

(51) Int. Cl.
*A01H 5/00* (2006.01)

(52) U.S. Cl. ..... Plt./133
(58) Field of Classification Search ..... Plt./33
See application file for complete search history.

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct variety of Hybrid Tea rose plant is provided which abundantly forms on a substantially continuous basis attractive elegant long-lasting double white blossoms wherein the blossom petals of a mature blossom tend to enclose the central portion of the blossom. The new variety is a spontaneous mutation of unknown causation of the 'Meivamo' variety (U.S. Plant Pat. No. 8,619). The plant exhibits a vigorous and upright growth habit, and strong and vigorous dark green foliage with a glossy aspect. No particular susceptibility to crytogamic diseases has been observed. The attractive dark green foliage contrasts nicely with the pure white blossom coloration. The new variety is well suited for cut flower production under greenhouse growing conditions. Excellent forcing has been observed particularly during the winter.

2 Drawing Sheets

Figure 1:
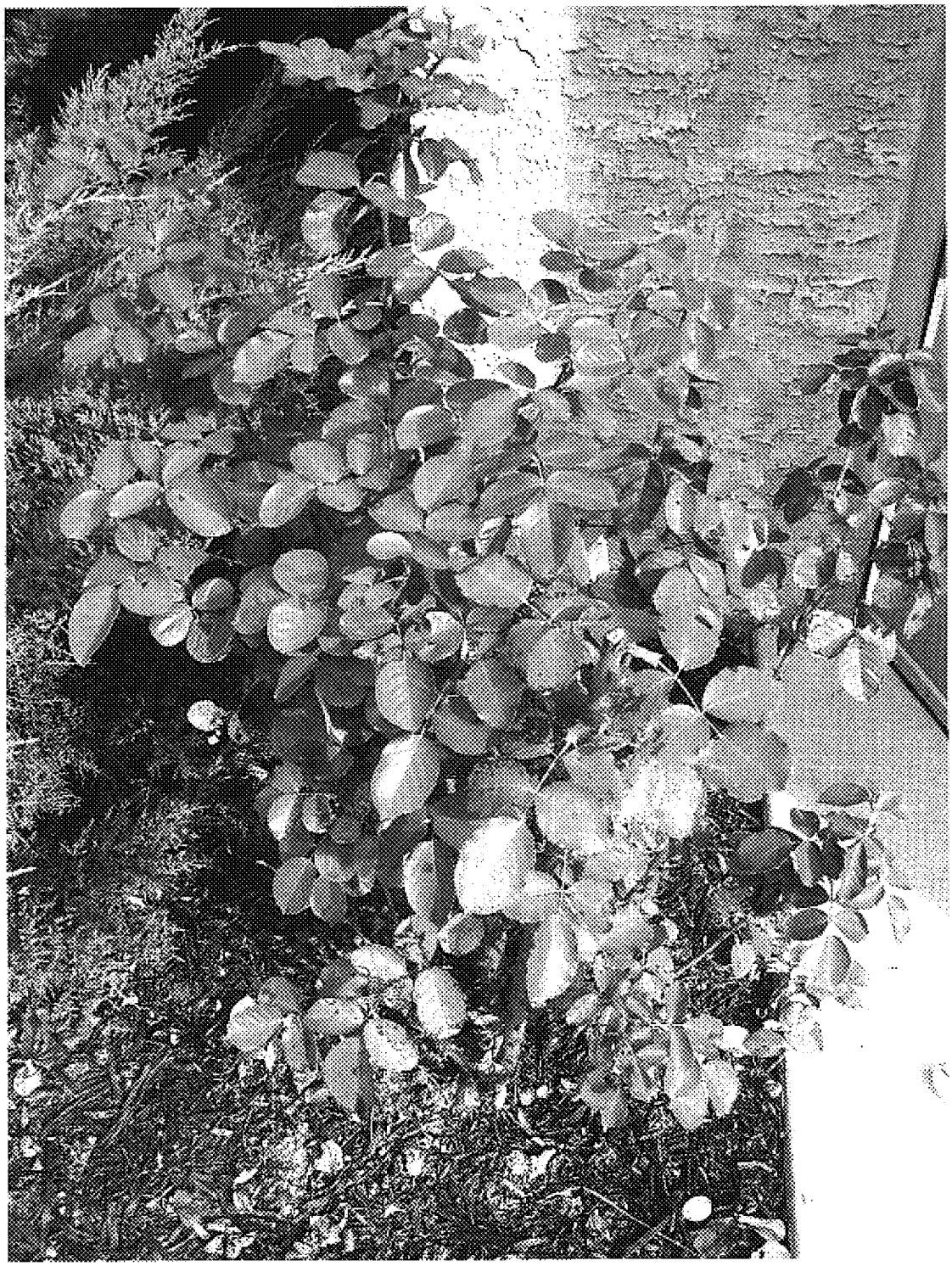

Botanical/commercial classification: *Rosa hybrida*/Hybrid Tea Rose.
Varietal denomination: cv. Meiwimova.

SUMMARY OF THE INVENTION

The new variety of *Rosa hybrida* Hybrid Tea rose plant was discovered at LeLuc, France, while growing among plants of the 'Meivamo' variety (U.S. Plant Pat. No. 8,619, granted Mar. 1, 1994). The new variety is a spontaneous whole plant mutation of unknown causation of the 'Meivamo' variety. I was primarily attracted to the new variety because of its distinctive blossom coloration. Had the new variety not been discovered and preserved by me it would have been lost to mankind.

The 'Meivamo' variety is a spontaneous mutation of the 'Keiromo' variety (U.S. Plant Pat. No. 7,138).

As discussed in U.S. Plant Pat. No. 7,138, the parent 'Keiromo' variety was the product of a controlled breeding program. The female parent (i.e., the seed parent) of the 'Keiromo' variety was the 'Jofitali' variety (U.S. Plant Pat. No. 4,083) and the male parent (i.e., the pollen parent) was the 'Happiness' variety (U.S. Plant Pat. No. 911). The parentage of the parent 'Keiromo' variety can be summarized as follows:

'Jofitali'×'Happiness'.

It was found that the new variety of the present invention (a) exhibits a vigorous and upright growth habit that is substantially identical to that of the 'Meivamo' variety (U.S. Plant Pat. No. 8,619), (b) forms in abundance elegant long-lasting double white blossoms wherein the blossom petals of a mature blossom tend to enclose the central portion of the blossom unlike the 'Meivamo' variety,
(c) forms strong and vigorous dark green glossy vegetation that contrasts well with the white blossom coloration,
(d) is well adapted for greenhouse forcing to produce cut flowers, and
(e) is not particularly affected by cryptogamic diseases.

The new variety well meets the needs of the horticultural industry and can be grown to advantage to produce cut flowers under greenhouse growing conditions. The blossoms are highly attractive and are formed in abundance on a substantially continuous basis. The ability of the plant to undergo forcing has been found to be excellent particularly during the winter.

The new variety can be readily distinguished from its 'Meivamo' parent. More specifically, the 'Meivamo' variety forms blossoms that are scarlet pink on the inside and light carmine rose on the outside. Also, the petals of the 'Meivamo' variety lack a propensity to enclose the central portion of the blossoms (i.e., the pistils and stamens) when the blossoms are mature.

The new variety of the present invention also can be readily distinguished from the 'Wekblunez' variety (U.S. Plant Pat. No. 16,572) and the 'Meifaissel' variety (U.S. Plant Pat. No. 16,951) through an inspection of the blossoms. More specifically, the 'Wekblunez' variety forms pink blossoms with a hint of lavender and the 'Meifaissel' variety displays smooth petal margins while the margins of the new variety commonly are slightly ruffled (i.e., wavey).

Additionally, the new variety of the present invention can be readily distinguished from its ancestors that produced the parent 'Meivamo' variety. The 'Jofitali' variety forms rose-bengal colored blossoms with a cardinal red center, and the 'Happiness' variety forms blossoms that are medium red in coloration.

The new variety has been found to undergo asexual propagation in France and in the United States, by a number of routes, including budding, grafting, and cuttage. Asexual propagation by the above-mentioned techniques at LeLuc, France and Wasco, Calif. U.S.A. has shown that the characteristics of the new variety are stable and are strictly transmissible by such asexual propagation from one generation to another.

The new variety has been named 'Meiwimova'.

BRIEF DESCRIPTION OF THE PHOTOGRAPH

The accompanying photograph of FIG. 1 shows as nearly true as it is reasonably possible to make the same, in a color illustration of this character, a typical specimen of the new variety. The rose plant of the new variety was approximately three years of age and was photographed during early November white budded on *Rosa indica* understock and growing outdoors at West Grove, Pa., U.S.A. Budding took place in California and for the first two years the plant was grown outdoors in California prior to shipment to Pennsylvania.

Figure 2:
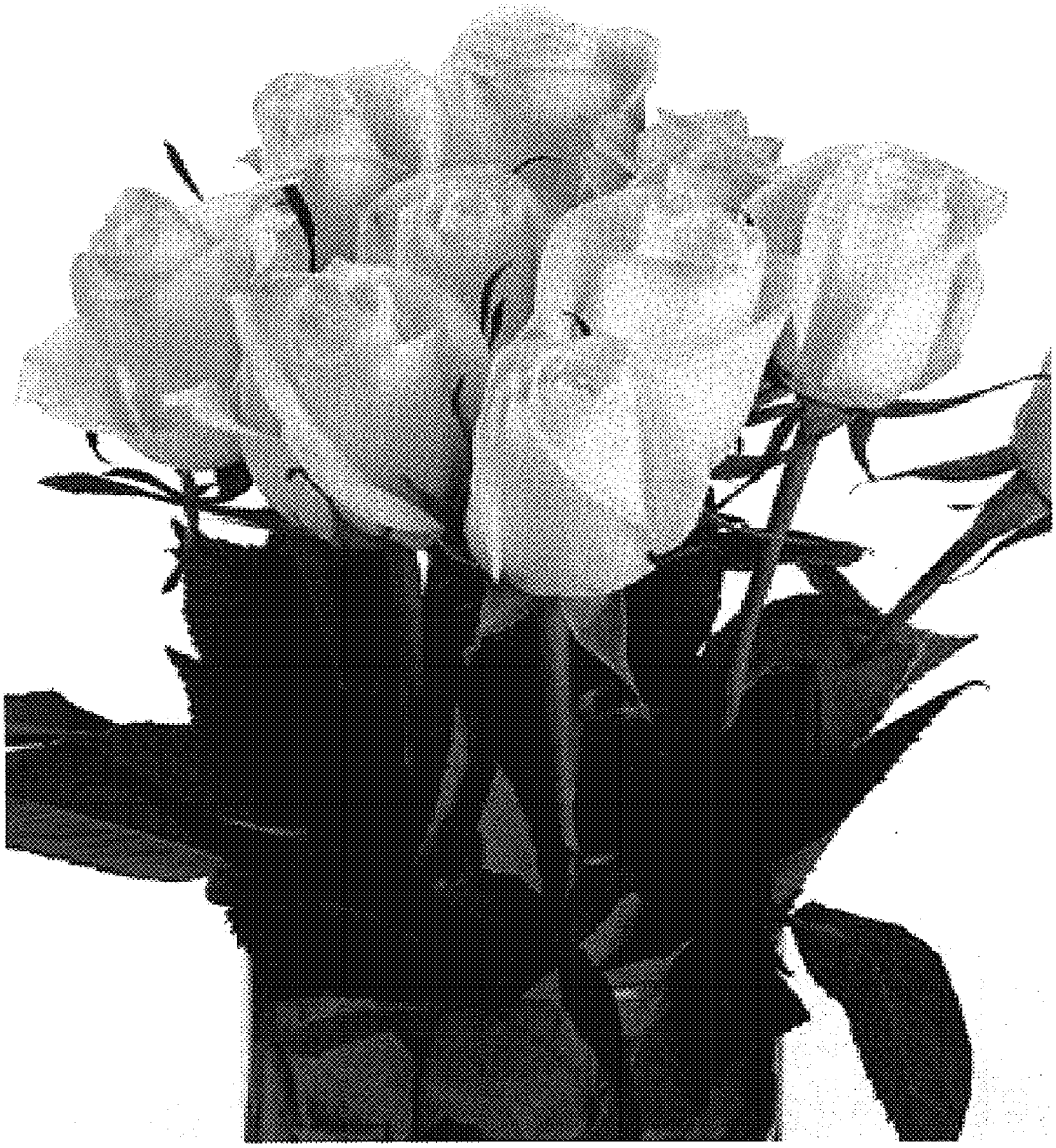

FIG. 2 shows typical blossoms and foliage of the new variety when cut and placed in a vase. The typical enclosure of the central portion of the blossoms by the petals is apparent.

DETAILED DESCRIPTION

The chart used in the identification of the colors is that of The Royal Horticultural Society (R.H.S. Colour Chart). The description is based on the observation of two year-old plants during October while budded on *Rosa indica* understock and growing in greenhouses at West Grove, Pa. U.S.A.

Class: Hybrid Tea.

Plant:

*Height.*—When pruned to a height of 85 cm, floral stems having a length of approximately 50 to 70 cm commonly are produced. When grown in the field at Wasco, Calif. U.S.A., a plant height of approximately 1.3 m commonly is observed at the end of the growing season.

*Width.*—Commonly approximately 1.3 m at the end of the growing season.

*Habit.*—Upright.

Branches:

*Color.*—Young stems: light green, generally smooth in texture, Green Group 143A and more or less shaded with some reddish coloration. Adult wood: medium green, slightly ribbed and generally smooth in texture, Green Group 137B.

*Thorns.*—Size: average, and commonly approximately 7 mm in length on average. Quantity: moderately numerous. Color: greenish near Yellow-Green Group 160B, on young stems and near Yellow-Orange Group 20B on mature wood.

Leaves:

*Stipules.*—Adnate, pectinate, fairly wide and linear, and common approximately 20 mm in length and approximately 9 mm in width.

*Petioles.*—Upper surface: Yellow-Green Group 145B commonly somewhat striped with reddish brown on young foliage and Yellow-Green Group 145A with glandular edges on adult foliage. Under surface: light green and bear a few thorns. Length: commonly approximately 25 mm on average. Diameter: commonly approximately 2 mm on average.

*Size.*—A seven-leaflet leaf commonly measures approximately 14 cm in length on average and approximately 10 cm in width on average.

*Leaflets.*—Number: 3, 5, and 7 (most often). Shape: generally oval. Apex: acute. Base: cuneate. Size: a terminal leaflet commonly is approximately 63 mm in length on average and approximately 36 mm in width on average. Serration: single and regular. Texture: commonly smooth and firm on both surfaces. General appearance: dense and glossy. Color (young foliage): upper surface: medium green, Green Group 137A. Under surface: light green, Green Group 137C, and commonly widely tinted with reddish-brown coloration. Color (adult foliage): upper surface: dark green, Green Group 139A Under surface: light green, Green Group 137C.

Inflorescence:

*Number of flowers.*—Commonly one flower per stem.

*Peduncle.*—Rigid, relatively straight, commonly near yellow-Green Group 144B in coloration, bears numerous light green aciculae, and the length commonly is approximately 11 to 12 cm on average.

*Sepals.*—Upper surface: tomentose and, generally near Yellow-Green Group 145D in coloration with Yellow-Green Group 145C at the margin. Under surface: approximately 25 mm in length on average, approximately 10 mm in width on average, commonly near Yellow-Green Group 145A in coloration and the edges of the outer sepals are glandular and slightly appendiculated.

*Buds.*—Shape: conical. Size: large. Length: approximately 4.5 cm on average. Color: Upper surface: Red Group 43C. Under surface: Red Group 43B.

*Flower.*—Shape: initially elongated, changing to cup-like with an apple-shaped center; and fully double. Diameter: approximately 12 to 13 cm on average. Color (when opening): Upper surface: White Group 155C. Under surface: White Group 155C. Color (when blooming): Upper surface: White Group 155C. Under surface: White Group 155C. Color (at end of blooming: Upper surface: White Group 155C. Under surface: White Group 155C. Fragrance: very slight. Lasting quality: commonly approximately 3 days on average on the plant and approximately 5 days on average when cut and placed in a vase. Petal number: approximately 32 to 35 on average under normal growing conditions. Petal shape: somewhat cordate and ruffled at the apex. Petal size: commonly approximately 30 mm in length on average and approximately 32 mm in width on average. Petal apex: obtuse. Petal base: obtuse. Petal margin: lower portion is entire and upper portion (approximately ¼ th) is undulate. Petal arrangement: petals tend to enclose the central portion of the blossoms when mature unlike the parent 'Meivamo' variety. Petal drop: fairly good with the petals commonly detaching cleanly before drying. Stamen number: approximately 234 on average. Petal texture: smooth and consistent. Anthers: normal in appearance and commonly near Orange Group 29C in coloration. Pollen: present and yellow-orange in coloration. Filaments: free-standing, commonly near Yellow Group 13D in coloration with fuschia tips, commonly approximately 8 mm in length on average, and common of irregular heights. Pistils: approximately 172 on average. Stigmas: normal in appearance, commonly near Yellow-Green Group 145A in coloration, and commonly located below the stamens. Styles: free-standing, near Yellow Group 12C in coloration, commonly approximately 7 mm in length on average, and commonly of irregular heights. Receptacle: commonly near Yellow Group 145A in coloration, fairly smooth, and in longitudinal section in the shape of a pitcher. Hips and seeds: none observed during observations to date.

Development:

*Vegetation.*—Strong and vigorous.

*Blooming.*—Abundant and substantially continuous when forced in a greenhouse for fresh-cut flower production.

*Resistance to diseases.*—Good with not particular susceptibility to cryptogamic diseases having been observed.

I claim:

1. A new and distinct Hybrid Tea rose plant characterized by the following combination of characteristics:

(a) exhibits a vigorous and upright growth habit that is substantially identical to that of the 'Meivamo' variety (U.S. Plant Pat. No. 8,619), (b) forms in abundance elegant long-lasting double while blossoms wherein the blossom petals of a mature blossom tend to enclose the central portion of the blossom unlike the 'Meivamo' variety, (c) forms strong and vigorous dark glossy green vegetation that contrasts well with the white blossom coloration, and (d) is well adapted for greenhouse forcing to produce cut flowers, and (e) is not particularly affected by cryptogramic diseases;

substantially as herein shown and described.

* * * * *